US006482828B1

(12) United States Patent
Uckun

(10) Patent No.: US 6,482,828 B1
(45) Date of Patent: Nov. 19, 2002

(54) 4-(4'-HYDROXYPHENYL) AMINO-6,7-DIMETHOXYQUINAZOLINE TO PREVENT DEVELOPMENT OF COLORECTAL CANCER

(75) Inventor: Fatih M. Uckun, White Bear Lake, MN (US)

(73) Assignee: Parker Hughes Institute, Roseville, MN (US)

( * ) Notice: Subject to any disclaimer, the term of this patent is extended or adjusted under 35 U.S.C. 154(b) by 0 days.

(21) Appl. No.: 10/145,639

(22) Filed: May 14, 2002

Related U.S. Application Data

(63) Continuation of application No. PCT/US00/31188, filed on Nov. 14, 2000.
(60) Provisional application No. 60/165,499, filed on Nov. 15, 1999.

(51) Int. Cl.⁷ ............................................. A61K 31/517
(52) U.S. Cl. .................................................... 514/266.4
(58) Field of Search ....................................... 514/266.4

(56) References Cited

U.S. PATENT DOCUMENTS 5,721,237 A   2/1998   Myers

FOREIGN PATENT DOCUMENTS

WO   99/61428   12/1999
WO   00/56720    9/2000

OTHER PUBLICATIONS

P. Goodman, et al.: "*Role of Tyrosine Kinase*" Journal of Biological Chemistry, vol. 273, No. 28 Jul. 10, 1998 (1948–07–10), pp. 17742–17748, XP002122432 American Society of Biological Chemists, Baltimore, MD, US ISSN: 0021–9258 p. 17742 –p. 17747.

Rama Krishna Narla: "*Inhibition of Human Glioblastoma Cell Adhesion*", Clinical Cancer Research, vol. 4, No. 10, Oct. 1998, pp. 2463–2471, XP002165068 the American Association for Cancer Research, US ISSN: 1078–0432, p. 2463 p. 2470.

F.M.Uckun: "*In Vivo Toxicity A. Pharmacokinetic Features of the Janus Kinase 3 Inhibitor Whip131.*" Clinical Cancer Research, vol. 5, Oct. 1999, pp. 2954–2962, XP002165069 the American Association for Cancer Research, US ISSN: 1078–0432 p. 2954 –page 2962.

Primary Examiner—Raymond Henley, III
(74) Attorney, Agent, or Firm—Merchant & Gould P.C.

(57) ABSTRACT

The present invention is directed to a method of preventing the development or recurrence of colorectal cancer in a mammal comprising administering to the mammal, an effective cancer preventative amount of 4-(4'-hydroxyphenyl)-amino-6,7-dimethoxyquinazoline or a pharmaceutically acceptable salt thereof.

20 Claims, No Drawings

4-(4'-HYDROXYPHENYL) AMINO-6,7-DIMETHOXYQUINAZOLINE TO PREVENT DEVELOPMENT OF COLORECTAL CANCER

This application is a continuation of PCT/US00/31188, filed on Nov. 14, 2000, published in English on May 25, 2001 as WO 01/36394, and designating the United States, which claims benefit of U.S. Provisional Application No. 60/165,499, filed on Nov. 15, 1999.

FIELD OF THE INVENTION

The present invention relates to quinazoline compounds, compositions and therapeutic methods for the treatment of cancers by administering quinazoline compounds.

BACKGROUND OF THE INVENTION

Currently, there is a need for methods useful for preventing the development or recurrence of cancer in mammals. Quinazoline compounds have been suggested as useful compounds in the treatment of cell growth and differentiation characterized by activity of the human epidermal growth factor receptor type2 (HER2). See, for example, Myers et.al., U.S. Pat. No. 5,721,237. Some quinazoline derivatives have been suggested as useful as anti-cancer agents for the treatment of specific receptor tyrosine kinase-expressing cancers, especially those expressing epithelial growth factor (EGF) receptor tyrosine kinase. See, for example, Barker et. al., U.S. Pat. No. 5,457,105. It is generally taught that quinazolines exert their anti-tumor effects via tyrosine kinase inhibition. However, while some quinazoline compounds inhibit the growth of tumor cells, such as brain tumor cells, others with equally potent tyrosine kinase inhibitory activity fail to do so (Naria et.al., 1998, *Clin. Cancer Res.* 4:1405–1414; Naria et.al., 1998, *Clin. Cancer Res.* 4:2463–2471).

Some quinazoline derivatives have also been suggested as useful agents for treating precancerous legions and inhibiting the growth of neoplastic cells. See for example, Pamukeu et al., U.S. Pat. Nos. 5,990,117; 6,037,345; and 6,046,206. Although many of the disclosed quinazoline derivatives are useful for treating precancerous legions and inhibiting the growth of neoplastic cells, there still exists the need to discover better compounds for the treatment of cancer, in particular colorectal cancer.

Cancer of the colon and/or rectum is now the third most common cause of death from cancer in the United States. Over 150,000 new cases of colon and/or rectal cancer are diagnosed each year. In addition, the incidence of colon cancer reportedly increases with age, particularly after the age of 40. Since the mean ages of populations in America and Western Europe are increasing, the prevalence of colorectal cancer should increase in the future.

To date, the only effective cure for colorectal cancer is surgery at an extremely early stage. Unfortunately, most cases of colorectal cancer are discovered too late for surgical cure. In many cases, the patient does not experience symptoms until the cancer has progressed to a malignant stage. The search for drugs useful for treating and preventing colorectal cancer continues.

What is needed in the art is a useful therapeutic agent for the treatment of colorectal cancer.

SUMMARY OF THE INVENTION

It has been discovered that 4-(4'-hydroxyphenyl)amino-6,7-dimethoxyquinazoline is effective as a therapeutic agent for the treatment of colorectal cancer. The present invention demonstrates the improved chemopreventive activity of 4-(4'-hydroxyphenyl)amino-6,7-dimethoxyquinazoline compared to known therapeutic agents.

The present invention provides a method of preventing the development or recurrence of colorectal cancer in a mammal comprising administering to the mammal, an effective cancer preventative amount of 4-(4'-hydroxyphenyl) amino-6,7-dimethoxyquinazoline, or a pharmaceutically acceptable salt thereof.

The present invention also provides the use of 4-(4'-hydroxyphenyl)amino-6,7-dimethoxyquinazoline, or a pharmaceutically acceptable salt thereof, to prepare a medicament useful for preventing the development or recurrence of colorectal cancer in a mammal.

These and other features and advantages of the present invention will become apparent after a review of the following detailed description of the disclosed embodiments and the appended claims.

DETAILED DESCRIPTION OF THE INVENTION

It has been discovered unexpectedly that 4-(4'-hydroxyphenyl)amino-6,7-dimethoxyquinazoline possesses increased activity against colorectal cancer. As such, 4-(4'-hydroxyphenyl)amino-6,7-dimethoxyquinazoline is particularly useful as an active agent for anticancer compositions and for methods of treating cancers, such as colorectal cancer.

Definitions

A number of terms are used throughout the present disclosure. Some of these terms are defined as shown below.

All scientific and technical terms used in this application have meanings commonly used in the art unless otherwise specified. As used in this application, the following words or phrases have the meanings specified.

As used herein, "pharmaceutically acceptable carrier" means any material which, when combined with 4-(4'-hydroxyphenyl)amino-6,7-dimethoxyquinazoline, allows 4-(4'-hydroxyphenyl)amino-6,7-dimethoxyquinazoline to retain biological activity, such as the ability to potentiate antibacterial activity of mast cells and macrophages. Examples include, but are not limited to, any of the standard pharmaceutical carriers such as a phosphate buffered saline solution, water, emulsions such as oil/water emulsions, and various types of wetting agents. Compositions comprising such carriers are formulated by well-known conventional methods (see, for example, Remington's Pharmaceutical Sciences, Chapter 43, 14th Ed., Mack Publishing Co., Easton, Pa.).

The term "conjugate" means a compound formed as a composite between two or more molecules. More specifically, in the present invention, 4-(4'-hydroxyphenyl) amino-6,7-dimethoxyquinazoline is bonded, for example, covalently bonded, to cell-specific targeting moieties forming a conjugate compound for efficient and specific delivery of 4-(4'-hydroxyphenyl)amino-6,7-dimethoxyquinazoline to a cell of interest.

The phrase "targeting moiety" means a molecule, which serves to deliver 4-(4'-hydroxyphenyl)amino-6,7-dimethoxyquinazoline to a specific site for the desired activity. Targeting moieties include, for example, molecules that specifically bind molecules on a specific cell surface. Such targeting moieties useful in the present invention include anti-cell surface antigen antibodies. Cytokines, including interleukins and factors such as granulocyte/macrophage stimulating factor (GMCSF) are also specific targeting moieties, known to bind to specific cells expressing high levels of their receptors.

The term "prodrug moiety" is a substitution group, which facilitates use of 4-(4'-hydroxyphenyl)amino-6,7-dimethoxyquinazoline, for example by facilitating entry of 4-(4'-hydroxyphenyl)amino-6,7-dimethoxyquinazoline into cells or administration of 4-(4'-hydroxyphenyl)amino-6,7-dimethoxyquinazoline. The prodrug moiety may be cleaved from 4-(4'-hydroxyphenyl)amino-6,7-dimethoxyquinazoline, for example by cleavage enzymes in vivo. Examples of prodrug moieties include phosphate groups, peptide linkers, and sugars, which moieties can be hydrolyzed in vivo.

As used herein, "inhibit" means to reduce by a measurable amount, or to prevent entirely.

As used herein, "to treat" means to inhibit or block at least one symptom that characterizes a pathologic condition, in a mammal threatened by, or afflicted with, the condition.

Compounds for Use in the Present Invention

Compounds for use in the present invention include 4-(4'-hydroxyphenyl)amino-6,7-dimethoxyquinazoline, or pharmaceutically acceptable salts thereof. Pharmaceutically acceptable salts of 4-(4'-hydroxyphenyl)amino-6,7-dimethoxyquinazoline may include organic acid addition salts formed with acids, which form a physiological acceptable anion, including, but not limited to, tosylate, methanesulfonate, acetate, citrate, malonate, tartarate, succinate, benzoate, ascorbate, a-ketoglutarate, and a-glycerophosphate. Suitable inorganic salts may also be formed, including, but not limited to, hydrochloride, sulfate, nitrate, bicarbonate, and carbonate salts.

Acceptable salts may be obtained using standard procedures well known in the art, for example by reacting a sufficiently basic compound such as an amine with a suitable acid affording a physiologically acceptable anion.

Synthesis of 4-(4'-hydroxyphenyl)amino-6,7-dimethoxyquinazoline 4-(4'-hydroxyphenyl)amino-6,7-dimethoxyquinazoline useful in the present invention may be synthesized from a key starting material, 4-chloro-6,7-dimethoxyquinazoline, prepared using published procedures (Nomoto, et al., 1990, Chem. Pharm. Bull., 38:1591–1595; Thomas, C. L., 1970, Academic Press, New York, N.Y., "I. Synthesis of quinazoline derivatives") as outlined below in Scheme 1 and as described more fully in the Examples below:

Scheme 1

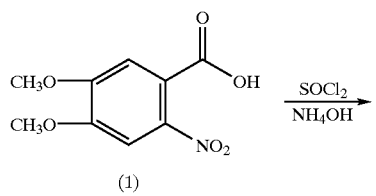

-continued

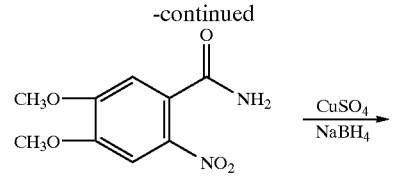

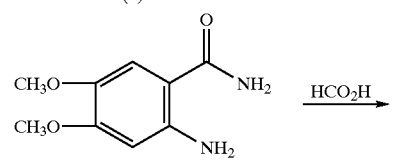

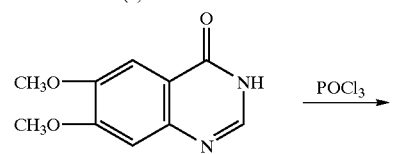

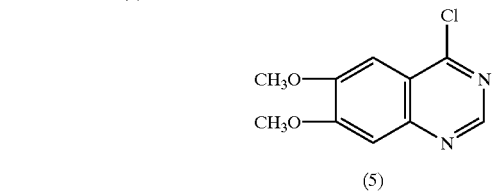

4-(4'-hydroxyphenyl)amino-6,7-dimethoxyquinazoline is then prepared by the condensation of 4-chloro-6,7-dimethoxyquinazoline with 4-aminophenol as outlined below in Scheme 2:

Scheme 2

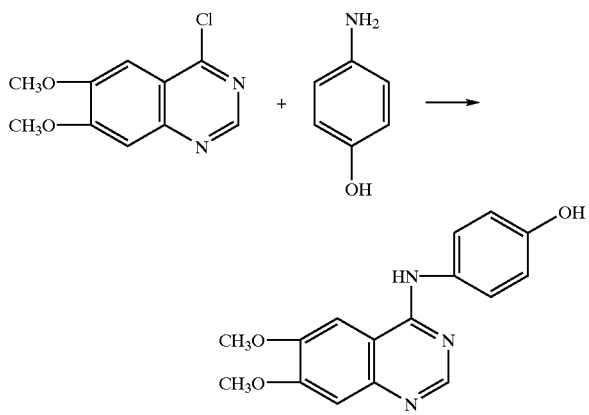

Compositions useful in the Present Invention 4-(4'-hydroxyphenyl)amino-6,7-dimethoxyquinazoline may be useful as a pharmaceutical composition prepared with a therapeutically effective amount of 4-(4'-hydroxyphenyl)amino-6,7-dimethoxyquinazoline and a pharmaceutically acceptable carrier or diluent.

4-(4'-hydroxyphenyl)amino-6,7-dimethoxyquinazoline may be formulated as a pharmaceutical composition and administered to a mammalian host, such as a human patient, in a variety of forms adapted to the chosen route of administration, i.e., orally or parenterally, by intravenous, intramuscular, topical or subcutaneous routes.

Thus, 4-(4'-hydroxyphenyl)amino-6,7-dimethoxyquinazoline may be systemically administered, e.g., orally, in combination with a pharmaceutically acceptable vehicle such as an inert diluent or an assimilable edible carrier, or by inhalation or insufflation. The components may be enclosed in hard or soft shell gelatin capsules, may be compressed into tablets, or may be incorporated directly with the food of the patient's diet. For oral therapeutic administration, 4-(4'-hydroxyphenyl)amino-6,7-dimethoxyquinazoline may be combined with one or more excipients and used in the form of ingestible tablets, buccal tablets, troches, capsules, elixirs, suspensions, syrups, wafers, and the like. 4-(4'-hydroxyphenyl)amino-6,7-dimethoxyquinazoline may be combined with a fine inert powdered carrier and inhaled by the subject or insufflated. Such compositions and preparations preferably contain at least 0.1 wt % of 4-(4'-hydroxyphenyl)amino-6,7-dimethoxyquinazoline. The percentage of 4-(4'-hydroxyphenyl)amino-6,7-dimethoxyquinazoline within a composition or preparation may, of course, be varied and may conveniently be between about 2 to about 60 wt % of a given unit dosage form. The amount of 4-(4'-hydroxyphenyl)amino-6,7-dimethoxyquinazoline in such therapeutically useful compositions is such that an effective dosage level will be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain 4-(4'-hydroxyphenyl)amino-6,7-dimethoxyquinazoline, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed.

In addition, 4-(4'-hydroxyphenyl)amino-6,7-dimethoxyquinazoline may be incorporated into sustained-release preparations and devices. Further, 4-(4'-hydroxyphenyl)amino-6,7-dimethoxyquinazoline may be administered intravenously or intraperitoneally by infusion or injection. Solutions of 4-(4'-hydroxyphenyl)amino-6,7-dimethoxyquinazoline may be prepared in water, optionally mixed with a nontoxic surfactant. Dispersions may also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion may include sterile aqueous solutions or dispersions or sterile powders comprising 4-(4'-hydroxyphenyl)amino-6,7-dimethoxyquinazoline, which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle may be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity may be maintained, for example, by the formation of liposomes, by the maintenance of the required particle size in the case of dispersions or by the use of surfactants. The prevention of the action of microorganisms may be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions may be brought about by the use in the compositions of agents delaying absorption, for example, aluminum monostearate and gelatin. Sterile injectable solutions may be prepared by incorporating 4-(4'-hydroxyphenyl)amino-6,7-dimethoxyquinazoline in the required amount in the appropriate solvent with various of the other ingredients enumerated above, as required, followed by filter sterilization. In the case of sterile powders for the preparation of sterile injectable solutions, the preferred methods of preparation are vacuum drying and freeze drying techniques, which yield a powder of 4-(4'-hydroxyphenyl)amino-6,7-dimethoxyquinazoline plus any additional desired ingredient present in the previously sterile-filtered solutions.

Useful solid carriers include finely divided solids such as talc, clay, microcrystalline cellulose, silica, alumina and the like. Other solid carriers include nontoxic polymeric nanoparticles or microparticles. Useful liquid carriers include water, alcohols or glycols or water-alcohol/glycol blends, in which 4-(4'-hydroxyphenyl)amino-6,7-dimethoxyquinazoline can be dissolved or dispersed at effective levels, optionally with the aid of non-toxic surfactants.

Generally, the concentration of 4-(4'-hydroxyphenyl)amino-6,7-dimethoxyquinazoline in a liquid composition will be from about 0.1 to about 25 wt %, preferably from about 0.5 to about 10 wt %. The concentration of 4-(4'-hydroxyphenyl)amino-6,7-dimethoxyquinazoline in a semi-solid or solid composition such as a gel or a powder will be about 0.1 to about 5 wt %, preferably about 0.5 to about 2.5 wt %.

Dosage Of 4-(4'-hydroxyphenyl)amino-6,7-dimethoxyquinazoline

The amount of 4-(4'-hydroxyphenyl)amino-6,7-dimethoxyquinazoline required for use in a given treatment will vary depending on a number of factors including, but not limited to, the route of administration, the nature of the condition being treated, and the age and condition of the patient. The amount of a given dosage will be ultimately at the discretion of the attendant physician or clinician. In general, however, a suitable dose will be in the range of from about 0.1 mg/kg to about 100 mg/kg of body weight per day. Preferably, the dose will range from about 10 to about 75 mg/kg of body weight per day, more preferably from about 3 to about 50 mg/kg of body weight per day, even more preferably from about 6 to about 90 mg/kg of body weight per day, and even more preferably from about 15 to 60 mg/kg of body weight per day.

4-(4'-hydroxyphenyl)amino-6,7-dimethoxyquinazoline is conveniently administered in unit dosage form; for example, containing from about 5 to about 1000 mg, preferably from about 10 to about 750 mg, and more preferably from about 50 to about 500 mg of active ingredient per unit dosage form.

Ideally, 4-(4'-hydroxyphenyl)amino-6,7-dimethoxyquinazoline is administered to achieve peak plasma concentrations of from about 0.5 to about 75 $\mu$M, preferably from about 1 to about 50 $\mu$M, and more preferably from about 2 to about 30 $\mu$M. This may be achieved, for example, by the intravenous injection of a 0.05 to 5 wt % solution of 4-(4'-hydroxyphenyl)amino-6,7-dimethoxyquinazoline, optionally in saline, or orally administered as a bolus containing about 1 to 100 mg of 4-(4'-hydroxyphenyl)amino-6,7-dimethoxyquinazoline. Desirable blood levels may be maintained by continuous infusion to provide about 0.01 to about 5.0 mg/kg/hr or by intermittent infusions containing from about 0.4 to about 15 mg/kg of 4-(4'-hydroxyphenyl)amino-6,7-dimethoxyquinazoline.

4-(4'-hydroxyphenyl)amino-6,7-dimethoxyquinazoline may conveniently be presented in a single dose or as divided doses administered at appropriate intervals, for example, as two, three, four or more sub-doses per day. The sub-dose itself may be further divided, e.g., into a number of discrete loosely spaced administrations, such as multiple inhalations from an insufflator.

Targeting 4-(4'-hydroxyphenyl)amino-6,7-dimethoxyquinazoline to Cells

In one aspect of the present invention, 4-(4'-hydroxyphenyl)amino-6,7-dimethoxyquinazoline may be targeted to cells where treatment is desired, in particular, to colorectal cells. 4-(4'-hydroxyphenyl)amino-6,7-dimethoxyquinazoline may be targeted to the desired cell by conjugation to a targeting moiety that specifically binds to the desired cell, thereby directing administration of a conjugated molecule. Useful targeting moieties are ligands, which specifically bind cell antigens or cell surface ligands, for example, antibodies against the B cell antigen, CD19 (such as B43) and the like.

To form conjugates for use in the present invention, targeting moieties are covalently bonded to sites on 4-(4'-hydroxyphenyl)amino-6,7-dimethoxyquinazoline. The targeting moiety, which is often a polypeptide molecule, is bound to 4-(4'-hydroxyphenyl)amino-6,7-dimethoxyquinazoline at reactive sites, including, but not limited to, OH, and the like. Specific linking agents are used to join the compounds. Preferred linking agents are chosen according to the reactive site to which the targeting moiety is to be attached.

Methods for selecting an appropriate linking agent and reactive site for attachment of the targeting moiety to 4-(4'-hydroxyphenyl)amino-6,7-dimethoxyquinazoline are known, and are described, for example, in Hermanson, et al., *Bioconjugate Techniques*, Academic Press, 1996; Hennanson, et al., *Immobilized Affinity Ligand Techniques*, Academic Press, 1992; and *Pierce Catalog and Handbook*, 1996, pp. T155–T201.

Measuring the Effectiveness of 4-(4'-hydroxyphenyl)amino-6,7-dimethoxyquinazoline The ability of 4-(4'-hydroxyphenyl)amino-6,7-dimethoxyquinazoline to prevent the development or recurrence of a cancer may be determined using pharmacological models, which are well known to the art, or using the methods as described herein. As used herein, preventing the development or recurrence includes both slowing the development or recurrence, as well as completely eliminating the development or recurrence.

The present invention is described above and further illustrated below by way of examples, which are not to be construed in any way as imposing limitations upon the scope of the invention. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

All chemicals used in the following Examples were purchased from the Aldrich Chemical Company, Milwaukee, Wis., and were used directly for synthesis. Anhydrous solvents such as acetonitrile, methanol, ethanol, ethyl acetate, tetrahydrofuran, chloroform, and methylene chloride were obtained from Aldrich as sure seal bottles under nitrogen and were transferred to reaction vessels by cannulation. All reactions were carried out under a nitrogen atmosphere.

Example 1

Synthesis of 4-(4'-hydroxyphenyl)amino-6,7-dimethoxyquinazoline

The key starting material, 4-chloro-6,7-dimethoxyquinazoline, was prepared using published procedures (Nomoto, et al., 1990, *Chem. Pharm. Bull.*, 38:1591–1595; Thomas, C. L., 1970, *Academic Press*, New York, N.Y., "I. Synthesis of quinazoline derivatives") as outlined below in Scheme 1 above.

Specifically, 4,5-dimethoxy-2-nitrobenzoic acid (compound 1) was treated with thionyl chloride to form acid chloride, followed by reacting with ammonia to yield 4,5-dimethoxy-2-nitrobenzamide (compound 2). Compound 2 was reduced with sodium borohydride in the presence of catalytic amounts of copper sulphate to give 4,5-dimethoxy-2-aminobenzamide (compound 3), which was directly refluxed with formic acid to yield 6,7-dimethoxyquinazoline-4(3H)-one (compound 4). Compound 4 was refluxed with phosphorus oxytrichloride to give 4-chloro-6,7-dimethoxyquinazoline (compound 5) in good yield.

4-(4'-hydroxyphenyl)amino-6,7-dimethoxyquinazoline was prepared by the condensation of 4-chloro-6,7-dimethoxyquinazoline with 4-aminophenol as outlined below in Scheme 2 above.

Specifically, a mixture of 4-chloro-6,7-dimethoxyquinazoline (448 mg, 2 mmols) and 4-aminophenol (2.5 mmols) in EtOH (20 ml) was heated to reflux. After refluxing for 4 to 24 hours, an excess amount of $Et_3N$ was added, and the solvent was concentrated to give the crude product which was recrystalized from DMF.

Example 2

Characterization of 4-(4'-hydroxyphenyl)amino-6,7-dimethoxyquinazoline 4-(4'-hydroxyphenyl)amino-6,7-dimethoxyquinazoline was synthesized as described in Example 1 and characterized. The structure is shown below, along with its identifying analytical test results. Proton and carbon Nuclear Magnetic Resonance ($^1$H and $^{13}$C NMR) spectra were recorded on a Mercury 2000 Varian spectrometer operating at 300 MHz and 75 MHz, respectively, using an automatic broad band probe. Unless otherwise noted, all NMR spectra were recorded in $CDCl_3$ at room temperature. $^1H$ chemical shifts are quoted in parts per million (d in ppm) downfield from tetramethyl silane (TMS), which was used as an internal standard at 0 ppm and s, d, t, q, m designate singlet, doublet, triplet, quartet and multiplet, respectively. Melting points were determined using a Fisher-Johns melting apparatus and are uncorrected. UV spectra were recorded using a Beckmann Model #DU 7400 UV/V is spectrometer with a cell path length of 1 cm. Methanol was used as the solvent for the UV spectra. Fourier Transform Infrared spectra were recorded using an FT-Nicolet model Protege #460 instrument. The infrared spectra of the liquid samples were run as neat liquids using KBr discs. The KBr pellet method was used for all solid samples. The GC/mass spectrum analysis was conducted using a Hewlett-Packard GC/mass spectrometer model #6890 equipped with a mass ion detector and Chem Station software. The temperature of the oven was steadily increased from 70° C. to 250° C. and the carrier gas was helium.

4-(4'-hydroxyphenyl)-amino-6,7-dimethoxyquinazoline

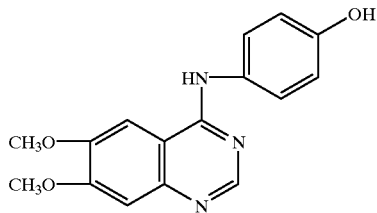

yield 84.29%; m.p. 245.0–248.0.° C.; UV(MeOH) $\lambda_{max}$: 203.0, 222.0, 251.0, 320.0 nm; IR(KBr) $v_{max}$: 3428, 2836, 1635, 1516, 1443, 1234 $cm^{-1}$; $^1H$ NMR(DMSO-$d_6$): 11.21 (s, 1H, —NH), 9.70(s, 1H, —OH), 8.74(s, 1H, 2-H), 8.22(s, 1H, 5-H), 7.40(d, 2H, J=8.9 Hz, 2',6'-H), 7.29(s, 1H, 8-H), 6.85(d, 2H, J=8.9 Hz, 3',5'-H), 3.98(s, 3H, —$OCH_3$), 3.97(s, 3H, —$OCH_3$); GC/MS m/z 298 ($M^+$+1, 100.00), 297($M^+$, 26.56), 296($M^+$−1, 12.46); Anal. ($C_{16}H_{15}N_3O_3$HCl) C, H, N.

Example 3

Administering 4-(4'-hydroxyphenyl)-amino-6,7-dimethoxyquinazoline to Mice

An $APC^{min}$ mouse model was used to test the ability of 4-(4'-hydroxyphenyl)-amino-6,7-dimethoxyquinazoline to prevent the development of colorectal cancer. A total of 23 $APC^{min}$ mice were fed rodent chow, which was supplemented with 0.3 wt % 4-(4'-hydroxyphenyl)-amino-6,7-dimethoxyquinazoline once a week starting at six weeks of age. A control group of 30 mice were fed rodent chow without 4-(4'-hydroxyphenyl)-amino-6,7-dimethoxyquinazoline. The health status of the mice was monitored for thirty weeks. Table 1 below describes the Probability of Survival for each group of mice over a period of 210 days.

TABLE 1

Probability Of Survival For Control Mice and $APC^{min}$ Mice

| Age (Days) | Control Mice (n = 30) | $APC^{min}$ Mice (n = 23) |
|---|---|---|
| 90 | 93 ± 5 | 100 ± 0 |
| 120 | 93 ± 5 | 94 ± 5 |
| 150 | 72 ± 9 | 81 ± 0 |
| 180 | 34 ± 10 | 68 ± 12 |
| 210 | 17 ± 8 | 68 ± 12 |

At thirteen weeks of age, 26% of the control mice developed rectal bleeding. Gross examination of the mice sacrificed at thirteen weeks of age revealed that 60% of the control mice showed polyps in the intestines. In contrast, at thirteen weeks of age, none of the $APC^{min}$ mice developed rectal bleeding or detectable polyps in the intestines.

By thirty weeks of age, only 17% of the control mice remained alive. However, 68% of the mice fed 4-(4'-hydroxyphenyl)-amino-6,7-dimethoxyquinazoline were still alive.

While a detailed description of the present invention has been provided above, the present invention is not limited thereto. The present invention described herein may be modified to include alternative embodiments, as will be apparent to those skilled in the art. All such alternatives should be considered within the spirit and scope of the present invention, as claimed below.

What is claimed is:

1. A method of treating a patient for colorectal cancer, wherein the method comprises:
   administering to the patient an effective amount of 4-(4'-hydroxyphenyl)-amino-6,7-dimethoxyquinazoline or a pharmaceutically acceptable salt thereof.

2. The method of claim 1, wherein the pharmaceutically acceptable salt contains one or more ions selected from tosylate, methanesulfonate, acetate, citrate, malonate, tartarate, succinate, benzoate, ascorbate, a-ketoglutarate, a-glycerophosphate, hydrochloride, sulfate, nitrate, bicarbonate, and carbonate.

3. The method of claim 1, wherein the effective amount is administered as a composition containing (a) a pharmaceutically acceptable carrier or diluent and (b) 4-(4'-hydroxyphenyl)-amino-6,7-dimethoxyquinazoline or a pharmaceutically acceptable salt thereof.

4. The method of claim 1, wherein the effective amount of 4-(4'-hydroxyphenyl)-amino-6,7-dimethoxyquinazoline or a pharmaceutically acceptable salt thereof is administered as a tablet, troch, pill, or capsule, which contains one or more of the following: a binder such as gum tragacanth, acacia, corn starch or gelatin; an excipient such as dicalcium phosphate; a disintegrating agent such as corn starch, potato starch, or alginic acid; a lubricant such as magnesium stearate; a sweetening agent such as sucrose, fructose, lactose, or aspartame; a flavoring agent such as peppermint, oil of wintergreen, cherry flavoring or orange flavoring; a liquid carrier such as a vegetable oil or a polyethylene glycol; a coating such as gelatin, wax, shellac or sugar; and a preservative such as methyl or propylparaben.

5. The method of claim 1, wherein the effective amount of 4-(4'-hydroxyphenyl)-amino-6,7-dimethoxyquinazoline or a pharmaceutically acceptable salt thereof is administered (a) via a sustained-release preparation or device; (b) intravenously; or (c) intraperitoneally.

6. The method of claim 1, wherein the effective amount of 4-(4'-hydroxyphenyl)-amino-6,7-dimethoxyquinazoline or a pharmaceutically acceptable salt thereof is administered as a solution containing one or more of the following: water; a nontoxic surfactant; glycerol; liquid polyethylene glycols;

triacetin; ethanol; vegetable oil; nontoxic glyceryl esters; antibacterial and antifungal agents such as parabens, chlorobutanol, phenol, sorbic acid, or thimerosal; isotonic agents such as sugars, buffers or sodium chloride; and absorption-delaying agents such as aluminum monostearate and gelatin.

7. The method of claim 1, wherein the effective amount of 4-(4'-hydroxyphenyl)-amino-6,7-dimethoxyquinazoline or a pharmaceutically acceptable salt thereof is targeted to colorectal cells by forming a conjugate molecule having a targeting moiety that specifically binds to the colorectal cells.

8. The method of claim 7, wherein the targeting moiety comprises a ligand or a polypeptide.

9. The method of claim 1, wherein the effective amount comprises from about 0.1 to about 100 mg of 4-(4'-hydroxyphenyl)-amino-6,7-dimethoxyquinazoline or a pharmaceutically acceptable salt thereof per kg of patient body weight.

10. The method of claim 1, wherein the effective amount of 4-(4'-hydroxyphenyl)-amino-6,7-dimethoxyquinazoline or a pharmaceutically acceptable salt thereof is administered to achieve a peak plasma concentration of from about 0.5 to about 75 $\mu$M.

11. The method of claim 1, wherein the patient is a mammal.

12. A method to prevent the development or recurrence of colorectal cancer in a patient, wherein the method comprises:

administering to the patient an effective amount of 4-(4'-hydroxyphenyl)-amino-6,7-dimethoxyquinazoline or a pharmaceutically acceptable salt thereof.

13. The method of claim 12, wherein the pharmaceutically acceptable salt contains one or more ions selected from tosylate, methanesulfonate, acetate, citrate, malonate, tartarate, succinate, benzoate, ascorbate, a-ketoglutarate, a-glycerophosphate, hydrochloride, sulfate, nitrate, bicarbonate, and carbonate.

14. The method of claim 12, wherein the effective amount is administered as a composition containing (a) a pharmaceutically acceptable carrier or diluent and (b) 4-(4'-hydroxyphenyl)-amino-6,7-dimethoxyquinazoline or a pharmaceutically acceptable salt thereof.

15. The method of claim 12, wherein the effective amount of 4-(4'-hydroxyphenyl)-amino-6,7-dimethoxyquinazoline or a pharmaceutically acceptable salt thereof is administered (a) via a sustained-release preparation or device; (b) intravenously; or (c) intraperitoneally.

16. The method of claim 12, wherein the effective amount of 4-(4'-hydroxyphenyl)-amino-6,7-dimethoxyquinazoline or a pharmaceutically acceptable salt thereof is targeted to colorectal cells by forming a conjugate molecule having a targeting moiety that specifically binds to the colorectal cells.

17. The method of claim 16, wherein the targeting moiety comprises a ligand or a polypeptide.

18. The method of claim 12, wherein the effective amount comprises from about 0.1 to about 100 mg of 4-(4'-hydroxyphenyl)-amino-6,7-dimethoxyquinazoline or a pharmaceutically acceptable salt thereof per kg of patient body weight.

19. The method of claim 12, wherein the effective amount of 4-(4'-hydroxyphenyl)-amino-6,7-dimethoxyquinazoline or a pharmaceutically acceptable salt thereof is administered to achieve a peak plasma concentration of from about 0.5 to about 75 $\mu$M.

20. The method of claim 12, wherein the patient is a mammal.

* * * * *